Jan. 21, 1969 E. B. LE GRICE Plant Pat. 2,856
ROSA FLORIBUNDA PLANT
Filed Jan. 6, 1967
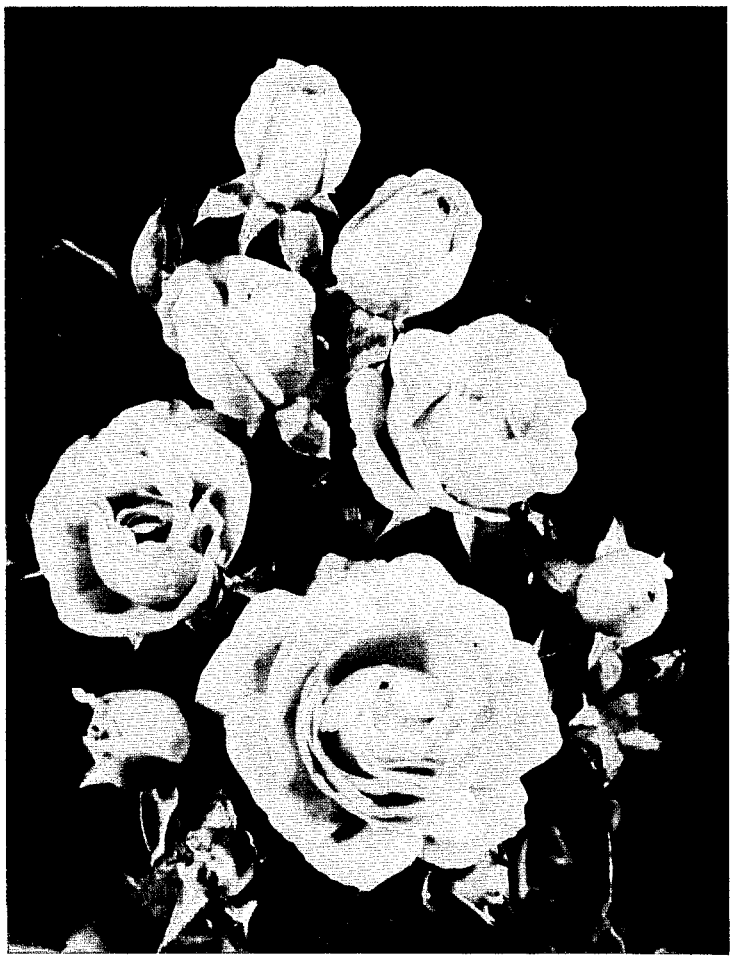
INVENTOR.
EDWARD BURTON LE GRICE
by: John H. Leonard,
his ATTORNEY.

United States Patent Office

Plant Pat. 2,856
Patented Jan. 21, 1969

2,856
ROSA FLORIBUNDA PLANT

Edward Burton Le Grice, North Walsham, Norfolk, England

Filed Jan. 6, 1967, Ser. No. 607,865
U.S. Cl. Plt.—28 1 Claim
Int. Cl. A01h 5/02

My invention relates to a new variety of floribunda rose plant.

The present rose plant was produced originally by me by crossing of an unknown seedling resulting from a cross between "Tantau's Triumph" and "Marjorie Le Grice," as the seed parent, and "Pimpernell," as the pollen parent. "Pimpernell" is a cross between an unnamed seedling as one parent, and a cross between "Poulsen's Pink" and "Golden Dawn" as the other parent. "Tantau's Triumph" is also known as "Cinnabar."

The new variety was crossed intentionally, in North Walsham, Norfolk, England, in 1959 by me by hand pollination in a hybridizing glass house.

The new variety has been asexually reproduced by me in 1959 at North Walsham, Norfolk, England by budding.

The drawing shows in color a number of typical stalks with leaves, buds, blooms and thorns.

The roots are of average size with a lateral spread ranging from the usual for rose plants to somewhat greater. The plant is generally deep rooted. The roots have good winter resistance when protected, and have withstood temperatures as low as 15° below zero Fahrenheit at Mentor, Ohio, without damage. Their resistance to drought is good and to wetness fair. The plant prefers a good, well drained, medium loam soil.

The exposed portion of the plant is in the form of a hardy, perennial, woody bush which is generally upright, symmetrical, and bushy with a somewhat flattened top. The plant grows generally to a height of about 2½ feet and to a width of about 2 to 2½ feet. It is a vigorous grower.

The exposed portion of the plant has good resistance to low temperatures when protected and fair to good resistance when unprotected. Its resistance to drought is good and wet seasons from fair to good.

For growth, it prefers moderate sun with a south and southwest exposure, preferably without shade. It thrives in normal, medium loam soil.

The main stalks of the plant are upright, much branched, stiff, and tough. They are adequate to support the foliage and blooms well.

The following color designations are from the British Color Council Horticultural Color Chart and are designated by sheet and number.

The stalks and branches range from Garnet Lake No. 828/1 for new growth to Lavender Green No. 862/1 for the old growth. The color is uniform in each instance.

The main stalks range from about 18 to 24 inches in length and are divergent. They have a smooth bark with sparse thorns. The branches are straight and short and adequate to support the foilage well.

The foliage in general is compact, the leaf arrangement being alternate. The leaves are average in quantity. The new leaves are Garnet Lake No. 828/1 on the top and bottom surfaces, and the old leaves are Sage Green No. 861 on the top surface and Lavender Green No. 761/1 on the bottom surface. This color arrangement is generally uniform.

The leaves are of average size, being a minimum of about six inches in length and having a minimum width of about 2 inches and maximum width of about 4 inches. The leaflets are well spaced and smaller than usual. They are pinnate with serrated margins with normal bases and apices. They are of medium thickness. They are smooth on the upper and lower faces. Their persistency on the plant is excellent. The leaves are slightly proportionately more narrow than usual.

The petioles or leaf stems are Lettuce Green No. 861/3. They average about one inch in length and are strong with a smooth surface texture.

The stipules are very pronounced Lettuce Green No. 861/3 with fimbriated edges of Garnet Lake No. 828/1.

The plant grows and blooms well in all temperate regions. It prefers sun, southern to western exposures, dry, well drained loam soil. The changes in exposure, drainage, and soil reduces slightly the quality and quantity of blooms, and result in a paler color. In very strong sunlight the blooms fade slightly.

The plant blooms continuously for a period of about five months. The flowers remain in good condition and also retain their color well when cut. When uncut, they pale slightly with age.

The buds are usual, being medium in size and globular. They have a smooth aspect and are supported upright on terminals and laterals.

When the sepals first divide, the petal color is deep Claret Rose No. 021. When the petals begin to unfurl and when half blown, they are Signal Red No. 719/1 on the top surface and Claret Rose No. 021 on the reverse surface.

The sepals are normal in shape but extend well beyond the bud.

The calyx is of normal size with a fuzzy texture and somewhat elongated.

The peduncles are strong and average from 1½ to 2½ inches in length, and for the entire flower head branch up to 10 inches. Their color is Willow Green ooo862 tinted with Garnet Lake No. 828/1.

The pedicels are strong and average from 1½ to 2½ inches in length, and are fuzzy. Their color is Willow Green No. ooo862 tinted with Garnet Lake No. 828/1.

The blooms open at normal rate. They average from 2 to 3 inches in diameter, and an average plant will bear from 75 to 100 blooms at the same time. The blooms are borne singly and in umbels. The permanence of the blooms is good both when cut and uncut.

Each bloom has about 30 petals. At the center of the blooms, the petals are Signal Red No. 719/1 on the upper surface and Claret Rose No. 021 on the under surface, both near the center and outer petals. The base of the petals is Signal Red No. 719/1, blending to Claret Rose No. 021 on the upper surface. The reverse of the petals is generally Claret Rose No. 021. The color of the petals on the upper surface is generally uniform throughout.

The general tonality of the blooming plant from a distance is China Rose No. 024. The blooms pale on opening in heat and on aging to a Claret Rose No. 021/2, ranging from a Signal Red No. 719/1 upon opening to Claret Rose No. 021/2 at about the third to fourth day.

The petals are thick. The arrangement of the petals is usual. They are iridescent in appearance on the upper faces with a matt finish or appearance on the under faces. They are generally smooth. There are few petaloids. The persistence of the petals is good when cut and uncut.

The blooms are of the usual shape during opening.

The fragrance of the blooms is faint.

The stamens are many and normal in shape and colored Spanish Orange No. o10. The filaments are short and the color of Sulphur Yellow No. 1/3 at the base and tinged at the upper portion with Garnet Lake No. 828/1.

The pollen is Yellow Ochre No. o7.

The styles are about ¼ inch in length and are Sulphur Yellow No. 1/2. The stigmas are very small and their color is Sulphur Yellow No. 1/2. The ovaries are plentiful.

The quantity of thorns on the main stalks is medium. They are relatively long and stiff. Their distribution is uneven on the main stalks. They are few in number and uneven on the laterals and absent on the peduncles. In color they are Garnet Lake No. 828/1. The plant appears to be adapted to all temperate zones throughout the world and medium loam soils.

The drawing further illustrates the characteristics of the clarity and the following tabulation is a detailed description of the new variety:

*General*

Parentage:
- *Seed parent.*—an unknown, a seedling which is a cross of Tantau's Triumph and Marjorie Le Grice.
- *Pollen parent.*—Pimpernell.

Classification: Botanic—*Rosa floribunda.*

Blooming habit: Location where observations were made—North Walsham, Norfolk, England.

Bud:
- *Size.*—Medium.
- *Form.*—Globular.
- *Aspect.*—Smooth.
- *Color.*—When sepals first divide, their color is deep Claret Rose No. 021. When they begin to unfurl and when they are half blown, they are Signal Red No. 719/1 on top and Claret Rose No. 021 on reverse.
- *Sepals.*—Normal shape but extend well beyond bud with fuzzy surface texture.
- *Calyx.*—Elongated relative to the remainder of the bud with fuzzy surface texture.
- *Peduncle.*—Strong, length from 1½ to 2½ inches.
- *Aspect.*—Fuzzy, Willow Green No. 000862 tinted with Garnet Lake No. 828/1.
- *Pedicels.*—Length—1½ to 2½ inches. Texture—fuzzy. Color, Willow Green No. 000862 tinted with Garnet Lake No. 828/1. Strong.
- *Opening.*—Normal.

Bloom:
- *Size.*—2 to 3 inches in diameter. Average blooms per plant, 75 to 100.
- *Borne.*—Singly and in umbels.
- *Stems.*—For whole flower head up to 10 inches. Strong with fuzzy aspect and few thorns.
- *Form.*—Usual.
- *Main stalks.*—Upright and much branched, relatively stiff and tough, adequate to support foliage in bloom. Ranges from 1½ to 2 inches from the ground up and divergent from the roots.
- *Branches.*—Relatively short and straight.
- *Permanence.*—Good both cut and uncut.

Petalage:
- *Texture.*—Thick.
- *Appearance.*—Iridescent on upper and inside and matt finish appearance on outside.
- *Form.*—Smooth.
- *Arrangement.*—Usual.
- *Petaloids.*—Few.
- *Persistence.*—Good, when cut and uncut.
- *Fragrance.*—Faint.
- *Lasting quality.*—Good.

Genital organs:
- *Stamens.*—Normal and numerous.
- *Color.*—Spanish Orange No. 10.

- *Filaments.*—Short.
- *Pollen.*—Yellow Ochre No. o7.
- *Styles.*—¼ inch. Color—Sulphur Yellow No. 1/2.
- *Stigmas.*—Very small, Sulphur Yellow No. 1/2.
- *Ovaries.*—Plentiful.

*Plant*

Form: A hardy, perennial, symmetrical woody bush of generally bushy and upright growth with a flattened top.

Growth: Vigorous. For a two year old plant, height about 2 to 2½ feet and width about 2 to 2½ feet.

Foliage: Alternate arrangement. Compact.
- *Leaf size.*—Average, being a maximum length of about six inches and width two to four inches.
- *Quantity.*—Average.
- *Color.*—New leaves, both top and bottom Garnet Lake No. 828/1. Old leaves, top surface Sage Green No. 861 and bottom surface, or reverse, Lavender Green No. 761/1.
- *Shape.*—Pinnate with serrated margins. Leaflets well spaced and smaller than usual.
- *Texture.*—Upper face — smooth. Lower face — smooth.
- *Persistency.*—Excellent.
- *Leaf characteristics.*—Medium thickness and proportionately slightly more narrow than usual.

Petioles: Length—about one inch. Smooth; strong. Color —Lettuce Green No. 861/3.

Stipules: Very pronounced Lettuce Green No. 861/3 with fimbriated edges of Garnet Lake No. 828/1, about one inch long.

Wood:
- *Newest growth.*—Garnet Lake No. 828/1.
- *Bark.*—Smooth between sparse thorns.
- *Old wood.*—Lavender Green No. 862/1.

Thorns:
- *Quantity.*—On main stalks and laterals—medium in quantity.
- *Form.*—Long, stiff, somewhat recurvent at outer ends; otherwise, generally in shape of equilateral triangle with one side concave and arcuate.
- *Color.*—Garnet Lake No. 821/1.
- *Position.*—Unevenly distributed on main stalks, few and uneven on laterals, and absent on peduncles.

The plant is characterized particularly by the luminous quality of the blooms and their color which make it most striking, both for outside and indoor decorations. It is particularly striking as a cut flower due to the large flower heads, bright color and lasting qualities when cut, and the fact that many blooms are at perfection in a blooming head at the same time. Further, important and distinguishing characteristics of the plant are the shape, quality and presentation of its blooms; its great freedom and even growth which make it ideal for medium height inside and outside bedding; the fact that the very thick flower stems support up to thirty flowers per truss; and its interestingly contrasting green wood and red thorns.

Having shown and described my new variety of floribunda plant and its manner of asexual reproduction, I claim:

1. The new and distinct variety of *Rosa floribunda* plant herein shown and described.

No references cited.

ROBERT E. BAGWILL, *Primary Examiner.*